US011555796B2

(12) United States Patent
Sasaki et al.

(10) Patent No.: US 11,555,796 B2
(45) Date of Patent: Jan. 17, 2023

(54) EVALUATION METHOD FOR THERMAL EXPANSION PROPERTIES OF TITANIA-CONTAINING SILICA GLASS BODY, AND MANUFACTURING METHOD FOR TITANIA-CONTAINING SILICA GLASS BODY

(71) Applicant: AGC Inc., Chiyoda-ku (JP)

(72) Inventors: Kazuya Sasaki, Fukushima (JP); Masaaki Takata, Fukushima (JP)

(73) Assignee: AGC Inc., Chiyoda-ku (JP)

( * ) Notice: Subject to any disclaimer, the term of this patent is extended or adjusted under 35 U.S.C. 154(b) by 183 days.

(21) Appl. No.: 16/910,227

(22) Filed: Jun. 24, 2020

(65) Prior Publication Data
US 2020/0319124 A1    Oct. 8, 2020

Related U.S. Application Data

(63) Continuation of application No. PCT/JP2018/046812, filed on Dec. 19, 2018.

(30) Foreign Application Priority Data

Dec. 25, 2017    (JP) ............................. JP2017-247630

(51) Int. Cl.
*G01N 25/16*    (2006.01)
*C03C 3/078*    (2006.01)
(Continued)

(52) U.S. Cl.
CPC .............. *G01N 25/16* (2013.01); *C03C 3/078* (2013.01); *G01J 3/44* (2013.01); *G01K 5/66* (2013.01);
(Continued)

(58) Field of Classification Search
CPC ........ G01N 25/16; G01N 29/07; G01N 29/11; G01N 2021/4735; G01N 2291/015;
(Continued)

(56) References Cited

U.S. PATENT DOCUMENTS

2005/0245382 A1*    11/2005    Iwahashi ................... C03C 3/06
501/54
2006/0276323 A1*    12/2006    Iwahashi ............. C03B 19/1415
501/54
(Continued)

FOREIGN PATENT DOCUMENTS

DE    10 2013 002 802 A1    8/2013
JP    2011-43503 A    3/2011
(Continued)

OTHER PUBLICATIONS

International Search Report dated Feb. 12, 2019 in PCT/JP2018/046812 filed Dec. 19, 2018, 2 pages.
(Continued)

*Primary Examiner* — Alexander Satanovsky
*Assistant Examiner* — Lyudmila Zaykova-Feldman
(74) *Attorney, Agent, or Firm* — Oblon, McClelland, Maier & Neustadt, L.L.P.

(57)    ABSTRACT

The present invention relates to a method for evaluating the thermal expansion properties of a titania-containing glass body. On the basis of measured values, obtained at a certain temperature, for a physical parameter that changes depending on the titania concentration and a physical parameter that changes depending on the fictive temperature, the thermal expansion coefficient of the titania-containing silica glass body and the slope of the thermal expansion coefficient are calculated using a linear relational expression represented by a plurality of physical properties. The thermal expansion properties of the titania-containing silica glass body are
(Continued)

evaluated on the basis of the calculated thermal expansion coefficient and thermal expansion coefficient slope.

8 Claims, 3 Drawing Sheets

(51) Int. Cl.
　　　G01J 3/44　　　(2006.01)
　　　G01K 5/66　　　(2006.01)
　　　G01N 29/07　　　(2006.01)
　　　G01N 29/11　　　(2006.01)
　　　G01N 21/47　　　(2006.01)

(52) U.S. Cl.
　　　CPC ............. *G01N 29/07* (2013.01); *G01N 29/11* (2013.01); *G01J 2003/4424* (2013.01); *G01N 2021/4735* (2013.01); *G01N 2291/015* (2013.01); *G01N 2291/0232* (2013.01); *G01N 2291/02809* (2013.01)

(58) Field of Classification Search
　　　CPC .. G01N 2291/0232; G01N 2291/02809; G01J 3/44; G01J 2003/4424; C03C 3/078; G01K 5/66
　　　See application file for complete search history.

(56) References Cited

U.S. PATENT DOCUMENTS

| | | | |
|---|---|---|---|
| 2010/0261597 A1* | 10/2010 | Koike | C03C 3/06 501/53 |
| 2011/0043787 A1 | 2/2011 | Duran | |
| 2012/0289393 A1* | 11/2012 | Kushibiki | G01N 29/221 501/53 |
| 2013/0103342 A1* | 4/2013 | Kushibiki | G01N 29/4472 702/136 |
| 2017/0241863 A1* | 8/2017 | Borrelli | G01N 21/65 |
| 2017/0328848 A1 | 11/2017 | Duran | |

FOREIGN PATENT DOCUMENTS

| | | |
|---|---|---|
| JP | 2013-199420 A | 10/2013 |
| JP | 5742833 B2 | 7/2015 |
| JP | 6020234 B2 | 11/2016 |
| WO | WO 2017/146922 A1 | 8/2017 |

OTHER PUBLICATIONS

Takeichi, Y. et al., "High-precision (<1ppb/° C.) Optical Heterodyne Interferometric Dilatometer for Determining Absolute CTE of EUVL Materials," Proc. of SPIE, vol. 6151, No. 61511Z, 2006, 8 pages.
Extended European Search Report dated Aug. 17, 2021 in European Patent Application No. 18895573.6, 11 pages.

* cited by examiner

Temperature (°C)

Raman Shift (cm$^{-1}$)

EVALUATION METHOD FOR THERMAL EXPANSION PROPERTIES OF TITANIA-CONTAINING SILICA GLASS BODY, AND MANUFACTURING METHOD FOR TITANIA-CONTAINING SILICA GLASS BODY

TECHNICAL FIELD

The present invention relates to a method for evaluating thermal expansion properties of a titania-containing silica glass body and a method for manufacturing a titania-containing silica glass body.

BACKGROUND ART

A photomask or a mirror is used as an optical element for an exposure apparatus used for EUV lithography (EUVL). In these optical elements, a titania-containing silica glass body (hereinafter, also referred to as a "$TiO_2$—$SiO_2$ glass body") which is a material having low thermal expansion properties has been used. Furthermore, with an increase in the output power of the EUVL light source, there is a concern about a temperature rise in the optical elements and thus, a glass material with low thermal expansion, which shows zero-thermal expansion properties in a wider temperature range (i.e., temperature dependence of the thermal expansion properties is small) has been required. As such a glass material having excellent low-thermal expansion properties, the above-mentioned $TiO_2$—$SiO_2$ glass is known, and furthermore, a $TiO_2$—$SiO_2$ glass doped with fluorine has been proposed (e.g., see Patent Document 1).

In these glass materials, it is preferable when thermal expansion properties such as a coefficient of thermal expansion (CTE), a slope of the coefficient of thermal expansion (CTE-SLOPE), which is an index relating to the temperature dependence of the thermal expansion properties, and temperature at which the above-mentioned CTE becomes 0 ppb/° C. (Cross-over Temperature; hereinafter also referred to as COT) can be evaluated, because it is possible to judge whether the materials are suitable for a desired use or not.

Conventionally, evaluation of such thermal expansion properties has been performed by measuring a coefficient of thermal expansion at each temperature of a glass sample by using an absolute dilatometer such as a Fabry-Perot interferometer (e.g., Non-Patent Literature 1).

Moreover, it has been known that a fluorine-doped $TiO_2$—$SiO_2$ glass body has the CTE near zero over a wider temperature range as compared with the case of one that is not doped with fluorine. Furthermore, it has been also known that the CTE-SLOPE value of a fluorine-doped $TiO_2$—$SiO_2$ glass body at a specific temperature is related to the values of titania concentration, fluorine concentration, and fictive temperature in the glass material (e.g., see Patent Literature 2).

CITATION LIST

Patent Literature

Patent Literature 1: Japanese Patent No. 5742833
Patent Literature 2: Japanese Patent No. 6020234
Non-Patent Literature 1: Y. Takeichi, I. Nishiyama, and N. Yamada, "High-precision (<1 ppb/° C.) Optical Heterodyne Interferometric Dilatometer for Determining Absolute CTE of EUVL Materials," Proc. SPIE, Vol. 6151, 61511Z (2006)

SUMMARY OF INVENTION

Technical Problem

However, the measurement by the Fabry-Perot interferometer as in Non-Patent Literature 1 requires a sample having a predetermined shape as a measurement sample, and a product for EUVL cannot be directly measured. Therefore, at present, an evaluation sample having a correlation with the product property values is sampled from the vicinity of the product, and the evaluation sample is measured to assure physical property values such as CTE, CTE-SLOPE, and COT.

Therefore, the physical property values of the product cannot be directly measured, and there is a fear that the physical property values are different between the actual product and the physical property value-assuring sample owing to deviation in the sampling position. In addition, processing such as precision-processing and reflection-coating is required for the measurement sample, and there is a problem that it takes time to obtain measurement results.

Accordingly, an object of the present invention is to provide a method for evaluating thermal expansion properties in a titania-containing silica glass body, which can easily evaluate the thermal expansion properties of a titania-containing silica glass body that is a low-expansion glass material, by a non-destructive measurement.

Solution to Problem

The method for evaluating thermal expansion properties of a titania-containing silica glass body of the present invention contains: a measurement step of each non-destructively measuring, for the titania-containing silica glass body, a physical parameter that fluctuates depending on a titania concentration and a physical parameter that fluctuates depending on a fictive temperature, at a predetermined temperature Tx, to obtain measured values of a plurality of physical parameters; a calculation step of calculating a coefficient of thermal expansion of the titania-containing silica glass body and a slope of the coefficient of thermal expansion of the titania-containing silica glass based on the measured values of the plurality of physical parameters obtained, respectively by using a linear relational expression expressed by the plurality of physical parameters; and an evaluation step of evaluating the thermal expansion properties of the titania-containing silica glass body based on the calculated coefficient of thermal expansion and slope of the coefficient of thermal expansion.

The method for manufacturing a titania-containing silica glass of the present invention contains: a molding step of molding a transparent titania-containing silica glass body to obtain a molded titania-containing silica glass body; an evaluation step of applying the method for evaluating thermal expansion properties of the present invention to the molded titania-containing silica glass body and evaluating whether at least one of the following requirements is satisfied or not: the coefficient of thermal expansion falls within a specific prescribed value range and the slope of the coefficient of thermal expansion is a specific prescribed value or less; and a judgment step of determining the glass body to be an acceptable product in a case where at least one of the requirements described above is satisfied in the evaluation step.

Advantageous Effects of Invention

According to the method for evaluating a titania-containing silica glass of the present invention, thermal expansion properties of a target titania-containing silica glass body, such as CTE, CTE-SLOPE and COT can be evaluated by non-destructive measurement at an arbitrary position in a parallel plane. Therefore, especially for products such as optical materials for an EUVL exposure apparatus, thermal expansion properties of the products can be directly evaluated.

According to the method for manufacturing a titania-containing silica glass of the present invention, a titania-containing silica glass body can be manufactured with selecting a glass body suitable as a product, for example, a glass body suitable for EUVL use application.

DESCRIPTION OF EMBODIMENTS

Hereinafter, the present invention will be described with reference to embodiments, but the present invention is not limited thereto.

[Method for Evaluating Thermal Expansion Properties of Titania-Containing Silica Glass Body]

A method for evaluating thermal expansion properties of a $TiO_2$—$SiO_2$ glass body according to an embodiment of the present invention will be described in detail below.

[Titania-Containing Silica Glass Body]

The titania-containing silica glass body ($TiO_2$—$SiO_2$ glass body) that is an object to be evaluated in the present embodiment is a $TiO_2$—$SiO_2$ glass body containing silica ($SiO_2$) and titania ($TiO_2$) as main components. The $TiO_2$—$SiO_2$ glass body is usually a $TiO_2$—$SiO_2$ glass body manufactured as an optical element for EUVL, but may be one to be used for other use applications.

Figure 1:
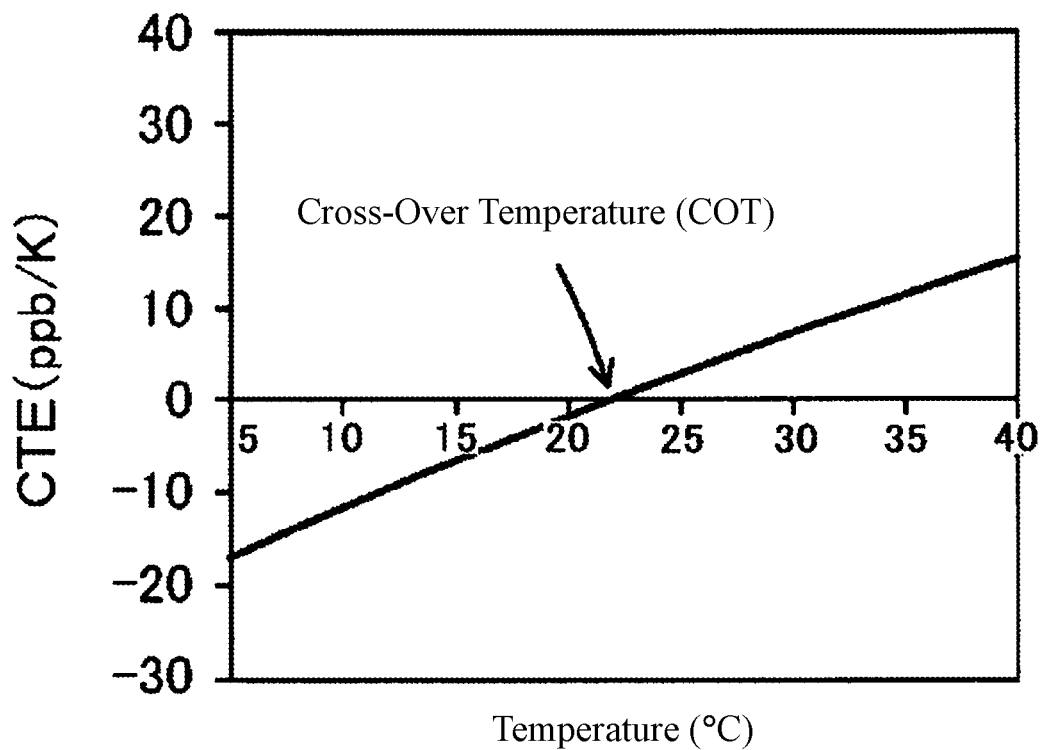
FIG. 1 is a graph showing temperature dependence of the coefficient of thermal expansion of a typical $TiO_2$—$SiO_2$ glass body.

A $TiO_2$—$SiO_2$ glass body is generally known as a low-thermal expansion material having a lower coefficient of thermal expansion (CTE) than that of common synthetic quartz glass. As for the $TiO_2$—$SiO_2$ glass body, CTE can be controlled by the $TiO_2$ content in the glass. Therefore, the $TiO_2$—$SiO_2$ glass body shows, for example, a relationship between the temperature and the coefficient of thermal expansion as shown in FIG. 1 and is useful as a glass having a very small coefficient of thermal expansion in the vicinity of room temperature (zero-expansion glass). Incidentally, in the present specification, the "zero-expansion glass" refers to a glass having a coefficient of thermal expansion where CTE becomes a value very close to zero (e.g., 0±5 ppb/° C.) at any temperature in the range of 0 to 60° C.

Furthermore, the $TiO_2$—$SiO_2$ glass body may be one doped with fluorine. A fluorine-doped $TiO_2$—$SiO_2$ glass body is more preferred in the case of being used for EUVL use applications because it has CTE being near zero over a wider temperature range than one that is not doped with fluorine.

Here, examples of the $TiO_2$—$SiO_2$ glass body includes a glass body having a composition of 91 to 95% by mass of $SiO_2$ and 5 to 9% by mass of $TiO_2$ based on oxides.

Moreover, examples of the fluorine-doped $TiO_2$—$SiO_2$ glass body includes a glass body having a composition of 85 to 95% by mass of $SiO_2$, 5 to 9% by mass of $TiO_2$, and 0 to 60,000 ppm by mass of F based on oxides.

It is preferable that the titania-containing silica glass body has at least one pair of opposing parallel planes, one plane of the at least one pair of opposing parallel planes has an area of 200 $cm^2$ to 3,000 $cm^2$, and the distance between the one pair of opposing parallel planes is in a range of 0.5 cm to 15 cm.

In addition, the $TiO_2$—$SiO_2$ glass body has a characteristic that CTE-SLOPE, which is temperature dependence of the thermal expansion properties, decreases as temperature increases. Therefore, as the thermal expansion properties of an ultra-low-thermal expansion glass used for EUVL system, it is required that the CTE value in a specific temperature range is controlled to fall within a predetermined numerical range or the COT value is controlled to be in a predetermined range.

Furthermore, in recent years, with an increase in the output power of a light source in EUVL, there is a concern that the temperature of an optical material for EUVL will rise. As properties required for an ultra-low-thermal expansion glass, it is required to have not only CTE at a specific temperature but also low-thermal expansion properties in a wider temperature range. That is, there is a demand for a low-thermal expansion glass material in which temperature dependence of the thermal expansion properties is small in the vicinity of the temperature at which low-thermal expansion is required. This can prevent distortion of the substrate caused by a temperature gradient from generating in a photomask substrate for EUVL or a mirror substrate, and can also suppress deformation of a mask pattern printed on a silicon wafer.

Then, in the method for evaluating thermal expansion properties of a $TiO_2$—$SiO_2$ glass body in the present embodiment, it can be judged whether the glass body is useful for EUVL use applications or not by evaluating whether it satisfies or not the above-mentioned predetermined properties relating to thermal expansion properties. The evaluation and judgment can be performed by sequentially subjecting the $TiO_2$—$SiO_2$ glass body to be evaluated to the respective steps to be described below.

(Measurement Step)

First, a plurality of physical parameters relating to the values of the titania concentration, fluorine concentration and fictive temperature of the $TiO_2$—$SiO_2$ glass body as a measurement target are measured non-destructively. The physical parameters to be measured here are not particularly limited as long as they include a physical parameter that fluctuates depending on the titania concentration, a physical parameter that fluctuates depending on the fluorine concentration, and a physical parameter that fluctuates depending on the fictive temperature. That is, it is sufficient that the titania concentration, fluorine concentration and fictive temperature can be evaluated by the physical parameters to be measured, respectively.

In the case where it is known that fluorine is not doped in advance, the measurement of the physical parameter relating to the fluorine concentration may be omitted unless the physical parameter relates to another physical parameter.

Incidentally, even in the case where the physical parameter is measured, it can be ignored and there is no problem because the influence of fluorine does not reach.

Here, the titania concentration is the titania concentration in the $TiO_2$—$SiO_2$ glass body, and this concentration is a factor that affects the CTE value and the CTE-SLOPE value. Moreover, the fluorine concentration is a factor that affects the CTE value and the CTE-SLOPE value. Furthermore, the fictive temperature is a factor that affects the CTE value and the CTE-SLOPE value. Therefore, the thermal expansion properties can be indirectly evaluated by measuring physical parameters that fluctuate depending on the titania concentration and the fluorine concentration and physical parameters that fluctuate depending on the fictive temperature.

The fictive temperature is generally an index value of the temperature at which the glass body has transformed from a supercooled liquid to a glassy state, and fluctuates under the influence of the manufacturing method thereof, particularly the cooling rate. Since a difference in the fictive temperature affects the properties of the glass body even in the case of the same composition and relates to the thermal expansion properties, in the present embodiment, it is essential as a factor for evaluation.

Here, examples of the physical parameter that fluctuates depending on the fictive temperature include an ultrasonic wave propagation velocity in a glass body, a ratio of peak intensities at specific wavelengths in a Raman spectrum, an IR absorption peak wave number, and the like. With respect to such an ultrasonic wave propagation velocity, a Raman spectrum and an IR absorption peak wave number, a $TiO_2$—$SiO_2$ glass body to be evaluated can be measured non-destructively, and measured values of the physical parameters for evaluation can be obtained.

Specifically, the ultrasonic wave propagation velocity includes a longitudinal wave sound velocity ($V_L$) and a transverse wave sound velocity ($V_S$), which are measured with applying ultrasonic waves to a glass body. It is known that the ultrasonic wave propagation velocity fluctuates depending on the composition and fictive temperature of the glass body (e.g., see Japanese Patent No. 5742833, T. Wei, "Acoustic properties of silica glass doped with fluorine" Journal of Non-Crystalline Solids 321 (2003) 126-133, etc.).

The titania concentration, fluorine concentration and fictive temperature at a certain temperature of a $TiO_2$—$SiO_2$ glass body to be measured individually contribute to the ultrasonic wave propagation velocity. Therefore, the value of the ultrasonic wave propagation velocity can be used as a physical parameter for evaluating the titania concentration, fluorine concentration and fictive temperature.

Next, the ratio of peak intensities at specific wavelengths in a Raman spectrum will be described below.

Figure 2:
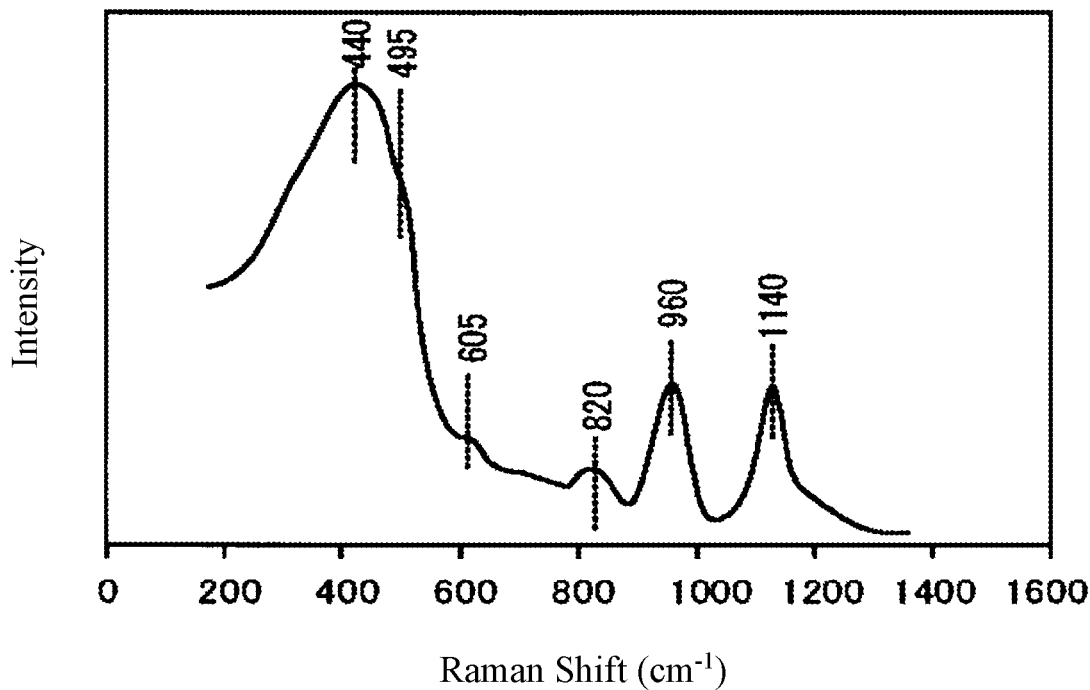
FIG. 2 is a Raman-scattering spectrum of a typical fluorine-doped $TiO_2$—$SiO_2$ glass body.

In a typical $TiO_2$—$SiO_2$ glass body doped with fluorine, a Raman scattering spectrum as shown in FIG. 2 is obtained in Raman spectroscopy. Such a Raman spectrum can be obtained by non-destructively measuring the $TiO_2$—$SiO_2$ glass body to be evaluated.

Among peaks of the spectrum obtained by Raman scattering light, the peaks having Raman shift values of 495 $cm^{-1}$ and 605 $cm^{-1}$ are peaks attributable to a four-membered ring structure and a three-membered ring structure in glass, respectively, and intensities of these peaks are denoted by $I_1$ and $I_2$, respectively. Further, the peaks at 440 $cm^{-1}$ and 820 $cm^{-1}$ are peaks attributable to the fundamental vibration between a silicon atom and an oxygen atom, and any of these peak intensities is denoted by $I_0$. The fictive temperature in a $TiO_2$—$SiO_2$ glass body has a linear relationship with the ratio ($I_1/I_0$ or $I_2/I_0$) of the scattering peak intensity of the four-membered ring structure or three-membered ring structure to the peak intensity of the fundamental vibration. Therefore, the fictive temperature can be evaluated by measuring the peak values in the Raman spectrum (e.g., see Japanese Patent No. 4085490, A. E. Geissberger, F. L. Galeener, "Raman studies of vitreous $SiO_2$ versus fictive temperature", Physical Review B vol. 28, Number 6, (1983) 3266-3271, etc.). Here, it is sufficient to include at least one of the peak intensity ratio ($I_1/I_0$) and the peak intensity ratio ($I_2/I_0$).

Examples of the physical parameter that fluctuates depending on the titania concentration include a ratio of peak intensities at specific wavelengths in a Raman spectrum, an ultrasonic wave propagation velocity, and the like.

Here, among peaks of the spectrum obtained by the Raman scattering light, the peaks having Raman shift values of 960 $cm^{-1}$ and 1,140 $cm^{-1}$ are peaks that fluctuate depending on the $TiO_2$ concentration in the glass, and intensities of these peaks are denoted by $I_3$ and $I_4$, respectively. Further, the peaks at 440 $cm^{-1}$ and 820 $cm^{-1}$ are peaks attributable to the fundamental vibration between a silicon atom and an oxygen atom, and any of these peak intensities is denoted by $I_0$. The $TiO_2$ concentration in the $TiO_2$—$SiO_2$ glass body has a linear relationship with the ratio ($I_3/I_0$ or $I_4/I_0$) of the peak intensity of the fundamental vibration between the silicon atom and the oxygen atom to the peak intensity of the fundamental vibration. Therefore, the titania concentration can be evaluated by measuring the peak values in the Raman spectrum (e.g., see G. Henderson, M. E. Fleet, "The structure of Ti silicate glasses by micro-Raman spectroscopy" The Canadian Mineralogist Vol. 33, pp. 399-408 (1995)).

Moreover, it is known that the peak position of the absorption spectrum in the vicinity of 2,260 $cm^{-1}$ in an IR transmission spectrum shifts depending on the fictive temperature, and thus the fictive temperature can be evaluated by measuring the IR transmission spectrum (e.g., see A. Agarwal et al., Journal of Non-Crystalline Solids, Vol. 185, p 191-198 (1995)).

Examples of the physical parameter that fluctuates depending on the fluorine concentration include a ratio of peak intensities at specific wavelengths in a Raman spectrum, an ultrasonic wave propagation velocity, and the like.

In the case where the $TiO_2$—$SiO_2$ glass body is doped with fluorine, the intensity (13) of the peak generated around 960 $cm^{-1}$ of the Raman scattering peaks fluctuates depending on the fluorine concentration in the glass body. Therefore, the fluorine concentration can be evaluated by considering the peak intensity ratio ($I_3/I_0$) described in the aforementioned titania concentration (e.g., see K. Awazu, H. Kawazoe, K. Muta, "Simultaneous generation of the 7.6-eV optical absorption band and F2 molecule in fluorine doped silica glass under annealing" Journal of Applied Physics 69, 4183 (1991) 4183-4188).

However, in this case, since one physical parameter contains a plurality of variable factors, it is necessary to take this point into consideration. Specifically, at the time of calculating linear relational expressions, when preparing physical parameters in a plurality of types of $TiO_2$—$SiO_2$ glass bodies, preferably, glass bodies in which values with regard to the factors to be taken into consideration are scattered in wide ranges are prepared and various types of glass bodies are used as glass bodies for derivation.

(Calculation Step)

Next, based on the measured values of the plurality of physical parameters obtained in the above-described measurement step, CTE of the $TiO_2$—$SiO_2$ glass body is calculated by a linear relational expression expressed by a plurality of physical parameters, and CTE-SLOPE of the TiO$_2$—SiO$_2$ glass body is calculated by a linear relational expression expressed by a plurality of physical parameters.

All of these linear relational expressions are derived in advance before the above-described measurement step, and the values of CTE and CTE-SLOPE can be easily calculated by applying the plurality of physical parameters measured in the measurement step to the derived linear relational expressions and performing calculation.

In deriving the linear relational expressions, first, as for the plurality of physical parameters to be measured in the above-described measurement step for the plurality of types of TiO$_2$—SiO$_2$ glass bodies, expressions relating to CTE and the plurality of physical parameters are established for each type of the glass body. Next, coefficients of the plurality of physical parameters are determined from the plurality of expressions based on regression calculation by the least-square method, to thereby derive one linear relational expression relating to CTE.

Similarly, as for the plurality of physical parameters to be measured in the above-described measurement step for the plurality of types of TiO$_2$—SiO$_2$ glass bodies, expressions relating to CTE-SLOPE and the plurality of physical parameters are established for each type of the glass body. Next, coefficients of the plurality of physical parameters are determined from the plurality of expressions based on regression calculation by the least-square method, to thereby derive one linear relational expression relating to CTE-SLOPE.

Here, the plurality of types of TiO$_2$—SiO$_2$ glass bodies can be considered as not only different types of glass bodies having different compositions but also those having the same composition but different fictive temperatures.

Hereinafter, the derivation of the linear relational expression will be described more specifically.

Here, described is a case where, as physical parameters, a physical parameter [A] that fluctuates depending on the fictive temperature, titania concentration and fluorine concentration, a physical parameter [B] that fluctuates depending on the fictive temperature, and a physical parameter [C] that fluctuates depending on the titania concentration are measured. As for the physical parameters for evaluating the properties of the fictive temperature, titania concentration and fluorine concentration, evaluation may be performed by providing one physical parameter for one property or evaluation may be performed by providing a plurality of physical parameters for one property. In the case where two or more properties overlap as one physical parameter, the evaluation may be performed collectively by using one physical parameter. However, in the case where two or more properties are expressed by one physical parameter, as for the properties relating thereto, physical parameters of the number of the properties or more should be prepared. It is preferable that one or more physical parameters are provided for one property as far as possible.

First, for the physical parameters [A] to [C], in accordance with the measurement temperature Tx in the above-described measurement step, a linear relational expression of the coefficient of thermal expansion at the temperature Tx (CTE at Tx) is established by using the physical parameters obtained by the measurement at the same temperature also in this step. This linear relational expression is represented, for example, by the following linear relational expression (1).

$$\text{CTE at } Tx \text{ [ppb/}°\text{ C.]} = a1[A] + b1[B] + c1[C] + d1 \quad (1), \text{ and}$$

(Here, in the expression, [A] is a term containing a longitudinal wave sound velocity $V_L$ or a transverse wave sound velocity $V_S$ in a TiO$_2$—SiO$_2$ glass body; [B] is a term containing $I_1/I_0$ or $I_2/I_0$ when the peak intensity at 440 cm$^{-1}$ or 820 cm$^{-1}$ is denoted by $I_0$, the scattered peak intensity at 495 cm$^{-1}$ is denoted by $I_1$, and the peak intensity at 605 cm$^{-1}$ is denoted by $I_2$, in the Raman spectrum in the TiO$_2$—SiO$_2$ glass body; [C] is a term containing $I_4/I_0$ when the peak intensity at 440 cm$^{-1}$ or 820 cm$^{-1}$ is denoted by $I_0$ and the peak intensity at 1,140 cm$^{-1}$ is denoted by $I_4$, in the Raman spectrum in the TiO$_2$—SiO$_2$ glass body; and a1, b1, c1, and d1 are coefficients calculated by regression calculation by the least-square method from the above linear relational expression (1).)

For a plurality of types of TiO$_2$—SiO$_2$ glass bodies, the physical parameters [A] to [C] are measured while fixing the measurement temperature Tx, and CTE at the temperature Tx is actually measured, to thereby establish a plurality of linear relational expressions (1) corresponding to the types of the glass bodies. At this time, the coefficients a1, b1, c1, and d1 still remain as they are as symbols.

Next, from the plurality of linear relational expressions (1) thus obtained, specific numerical values of the coefficients a1, b1, c1, and d1 are calculated by regression calculation using the least-square method, thereby deriving the linear relational expression (1) at the temperature Tx.

Then, for these physical parameters [A] to [C], in accordance with the measurement temperature Tx in the above-described measurement step, a linear relational expression at the temperature Tx (CTE-SLOPE at Tx) is established by using the physical parameters obtained by the measurement at the same temperature also in this step. This linear relational expression is represented, for example, by the following linear relational expression (2).

$$\text{CTE-SLOPE at } Tx \text{ [ppb/}°\text{ C.]} = a2[A] + b2[B] + c2[C] + d2 \quad (2)$$

(Here, in the expression, [A] is a term containing a longitudinal wave sound velocity $V_L$ or a transverse wave sound velocity $V_S$ in a TiO$_2$—SiO$_2$ glass body; [B] is a term containing $I_1/I_0$ or $I_2/I_0$ when the peak intensity at 440 cm$^{-1}$ or 820 cm$^{-1}$ is denoted by $I_0$, the scattered peak intensity at 495 cm$^{-1}$ is denoted by $I_1$, and the peak intensity at 605 cm$^{-1}$ is denoted by $I_2$, in the Raman spectrum in the TiO$_2$—SiO$_2$ glass body; [C] is a term containing $I_4/I_0$ when the peak intensity at 440 cm$^{-1}$ or 820 cm$^{-1}$ is denoted by $I_0$ and the peak intensity at 1,140 cm$^{-1}$ is denoted by $I_4$, in the Raman spectrum in the TiO$_2$—SiO$_2$ glass body; and a2, b2, c2, and d2 are coefficients calculated by regression calculation by the least-square method from the above linear relational expression (2).)

For a plurality of types of TiO$_2$—SiO$_2$ glass bodies, the physical parameters [A] to [C] are measured while fixing the measurement temperature Tx, and CTE-SLOPE at the temperature Tx is actually measured, to thereby establish linear relational expressions (2) corresponding to the types of the glass bodies. At this time, the coefficients a2, b2, c2, and d2 still remain as they are as symbols.

Next, from the plurality of linear relational expressions (2) thus obtained, specific numerical values of the coefficients a2, b2, c2, and d2 are calculated by regression calculation using the least-square method, thereby deriving the linear relational expression (2) at the temperature Tx. Tx is preferably 0 to 60° C., more preferably 5 to 50° C., and still more preferably 15 to 40° C., from the viewpoint of the temperature suitably used in EUV lithography.

(Evaluation Step)

Then, the thermal expansion properties of the $TiO_2$—$SiO_2$ glass body are evaluated based on the CTE value and the CTE-SLOPE value calculated in the calculation step.

In the evaluation of the thermal expansion properties, the calculated CTE value and CTE-SLOPE value may be independently evaluated, or may be evaluated in consideration of both. When these values are evaluated, a new reference value may be calculated and evaluated from CTE and CTE-SLOPE calculated at different measurement temperatures Tx. The evaluation may be performed in consideration of the properties of other $TiO_2$—$SiO_2$ glass bodies.

In the case where the evaluation is performed by using the CTE value, for example, the case where the calculated CTE value falls within a target range of CTE=$0\pm\Delta$ ($\Delta$ is an arbitrary real number) is determined to be acceptable, and the case where it falls outside of the range is determined to be unacceptable. $\Delta$ is preferably 5 ppb/K or less, and more preferably 3 ppb/K or less.

In the case where the evaluation is performed by using the CTE-SLOPE value, for example, the case where the calculated CTE-SLOPE value is smaller than a target value is determined to be acceptable, and the case where the value is larger is determined to be unacceptable. The target CTE-Slope value is preferably −2.5 ppb/K/K to 2.5 ppb/K/K, and more preferably −1.0 ppb/K/K to 1.0 ppb/K/K, from the viewpoint of obtaining low-thermal expansion over a wider temperature range.

Moreover, COT can be calculated and evaluated as a thermal expansion property by applying the linear relational expression (1) of CTE.

COT can be calculated by similarly determining the linear relational expression (1) for a plurality of temperatures. That is, at a plurality of different temperatures (e.g., n points of different temperatures such as Tx1, Tx2, Tx3, . . . , Txn are set as the measurement temperatures) as the measurement temperature Tx, the corresponding linear relational expressions CTE at Tx are determined in the number (n) of set temperatures.

In the $TiO_2$—$SiO_2$ glass body to be measured, n CTE values at the above-mentioned individual temperatures (Tx1 to Txn) are determined in the same manner as described above from the measured values of the plurality of physical parameters obtained in the measuring step. The determined n CTE values are fitted as a quadratic function of temperature, and a temperature $T_0$ at which CTE becomes 0 is determined from the quadratic function: CTE=$a3T^2+b3T+c3$, and is defined as COT.

[Method for Manufacturing Titania-Containing Silica Glass]

The method for manufacturing a titania-containing silica glass in the present embodiment includes: a molding step of molding a transparent titania-containing silica glass body to obtain a molded titania-containing silica glass body; an evaluation step of applying the above-described method for evaluating thermal expansion properties to the molded titania-containing silica glass body and evaluating whether at least one of the following requirements is satisfied or not: the coefficient of thermal expansion falls within a specific prescribed value range and the slope of the coefficient of thermal expansion is a specific prescribed value or less; and a judgment step of determining the glass body to be an acceptable product in the case where at least one of the requirements is satisfied in the evaluation step.

(Molding Step)

Here, the transparent titania-containing silica glass body can be obtained by a known method. Examples of this method include a direct method in which a silica precursor and a titania precursor are subjected to flame hydrolysis, deposited on a substrate, and then melted to perform vitrification, a so-called VAD (Vapor-Phase Axial Deposition) method in which a porous glass body obtained by flame hydrolysis of a silica precursor and a titania precursor is heated under an inert gas atmosphere to perform transparent vitrification, and the like. The glass body is then molded to a desired shape.

The obtained transparent titania-containing silica glass body is usually heated again, and further subjected to an annealing treatment of gradually cooling, thereby removing strain and adjusting the refractive index. Incidentally, the fictive temperature is also adjusted by this annealing step.

(Evaluation Step)

For the obtained transparent titania-containing silica glass body, the above-described method for evaluating thermal expansion properties of a titania-containing silica glass body is performed to evaluate whether at least one of the following requirements is satisfied or not: the thermal expansion coefficient falls within a specific prescribed value range and the slope of the coefficient of thermal expansion is a specific prescribed value or less.

In this evaluation, the case where the calculated CTE value and CTE-Slope value fall within the ranges of the target values of the desired transparent titania-containing silica glass body is determined to be acceptable and, the case where values fall outside of the ranges is determined to be unacceptable.

(Judgment Step)

Next, selection is performed by judging as an acceptable product when at least one requirement is satisfied in the above-described evaluation step and judging as an unacceptable product when none of the requirements is satisfied. The transparent titania-containing silica glass body judged as an acceptable product is used as a product as it is, and the transparent titania-containing silica glass body judged as an unacceptable product is not used as a product. The unacceptable product is preferably reused again as a raw material for manufacturing a transparent titania-containing silica glass body.

EXAMPLES

Hereinafter, the present invention will be described in more detail with reference to Examples, but the present invention is not limited to these Examples. The following simulated a method for evaluating CTE, CTE-SLOPE, and COT by non-destructive measurement.

<Calculation of Linear Relational Expressions>

As shown in Table 1, 11 sample numerical values having different titania concentrations, fluorine concentrations, and fictive temperatures were prepared for titania-containing silica glass. The CTE and CTE-SLOPE values at 22° C. are measured for these sample numerical values (actually measured values are shown in Table 2).

Moreover, for these samples, in order to derive the linear relational expression (1) described in the Detailed Description, an ultrasonic longitudinal wave propagation velocity serving as a physical parameter [A] can be measured at 22° C., and also a laser Raman spectrum can be measured to calculate scattering peak intensity ratios serving as physical parameters [B] and [C]. Table 1 summarizes these physical parameters.

TABLE 1

|  | Fluorine dope | [A] Longitudinal wave sound velocity $V_L$ (m/sec) | [B] Peak intensity ratio $I_2/I_0$ | [C] Peak intensity ratio $I_4/I_0$ |
|---|---|---|---|---|
| Sample 1 | No | 5779 | 0.028 | 6.29 |
| Sample 2 | No | 5760 | 0.028 | 7.41 |
| Sample 3 | No | 5799 | 0.033 | 5.19 |
| Sample 4 | No | 5779 | 0.044 | 7.12 |
| Sample 5 | No | 5813 | 0.049 | 5.56 |
| Sample 6 | Yes | 5678 | 0.017 | 6.13 |
| Sample 7 | Yes | 5725 | 0.025 | 6.07 |
| Sample 8 | Yes | 5699 | 0.026 | 6.10 |
| Sample 9 | Yes | 5707 | 0.022 | 6.95 |
| Sample 10 | Yes | 5632 | 0.015 | 7.67 |
| Sample 11 | Yes | 5640 | 0.012 | 7.25 |

When the linear relational expression (1) with respect to CTE and the linear relational expression (2) with respect to CTE-SLOPE were derived from the obtained physical parameters [A] to [C], the following linear relational expressions (E1) and (E2) were obtained.

$$\text{CTE at } 22°\text{C.} = 0.156[V_L] - 1695.58[I_2/I_0] - 40.68[I_4/I_0] - 547.98 \quad (E1)$$

$$\text{CTE-SLOPE at } 22°\text{C.} = 0.0066[V_L] + 16.68[I_2/I_0] + 0.1098[I_4/I_0] - 36 \quad (E2)$$

The actually measured values of CTE and CTE-SLOPE can be obtained by precisely measuring a coefficient of thermal expansion and a CTE-SLOPE value at 22° C. for thermal expansion in the longitudinal direction by using a molded glass body having a length of 100 mm and by using a laser heterodyne interference-type thermal expansion meter CTE-01 manufactured by Uniopt Corporation.

Furthermore, as for the ultrasonic longitudinal wave propagation velocity, the longitudinal wave sound velocity ($V_L$) can be measured by using an ultrasonic pulser-receiver MODEL 5073PR manufactured by Olympus Corporation. As the frequency of the longitudinal wave, 20 MHz can be used. In the measurement, while the temperature of a molded glass body having a length of 100 mm is kept constant (22° C.), a longitudinal ultrasonic wave is generated by the pulsar at one end of the glass material, and the time required for receiving the longitudinal ultrasonic wave that is propagated through the molded glass body and reflected at the other end, that is, the time required for reciprocation of the longitudinal wave sound velocity is measured. Then, the longitudinal wave sound velocity ($V_L$) can be easily calculated by dividing the propagation distance of the longitudinal ultrasonic wave by the time required for propagation.

The laser Raman spectrum can be obtained by first injecting a second harmonic of an Nd:YAG laser having a wavelength of 532 nm into the sample at a power of 5 W as an excitation light source for the Raman spectrum measurement and measuring a spectrum of Raman scattered light. Next, peak intensities at individual peak wavelengths of wavelength 605 cm$^{-1}$ ($I_2$), wavelength 820 cm$^{-1}$ ($I_0$) and wavelength 1,140 cm$^{-1}$ ($I_4$) were measured from the obtained Raman spectrum, and the peak intensity ratios $I_2/I_0$ and $I_4/I_0$ were calculated. Here, for the Raman spectroscopic measurement, a laser Raman spectrophotometer HQS-1000 manufactured by JASCO Corporation can be used.

Figure 3:
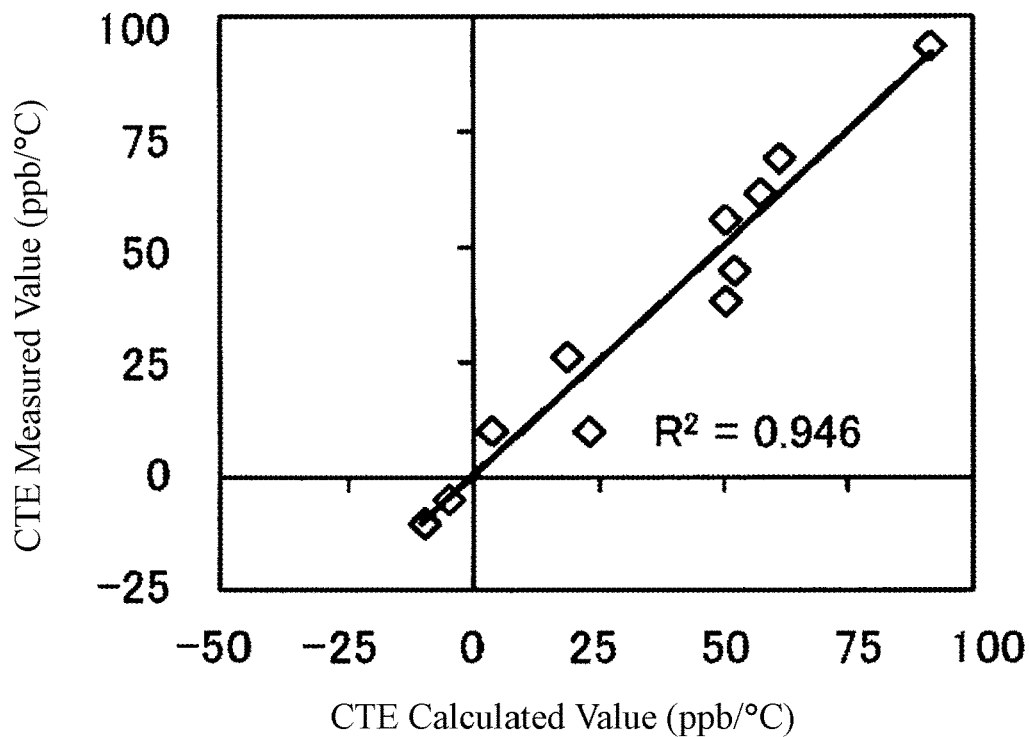
FIG. 3 is a graph showing a relationship between a calculated value of CTE calculated by using a linear relational expression and a measured value in Examples.

Table 2 shows the CTE value calculated from the linear relational expression (1) and the actually measured CTE value at 22° C., and FIG. 3 collectively shows the relationship between the calculated value and the actually measured value in a graph.

Figure 4:
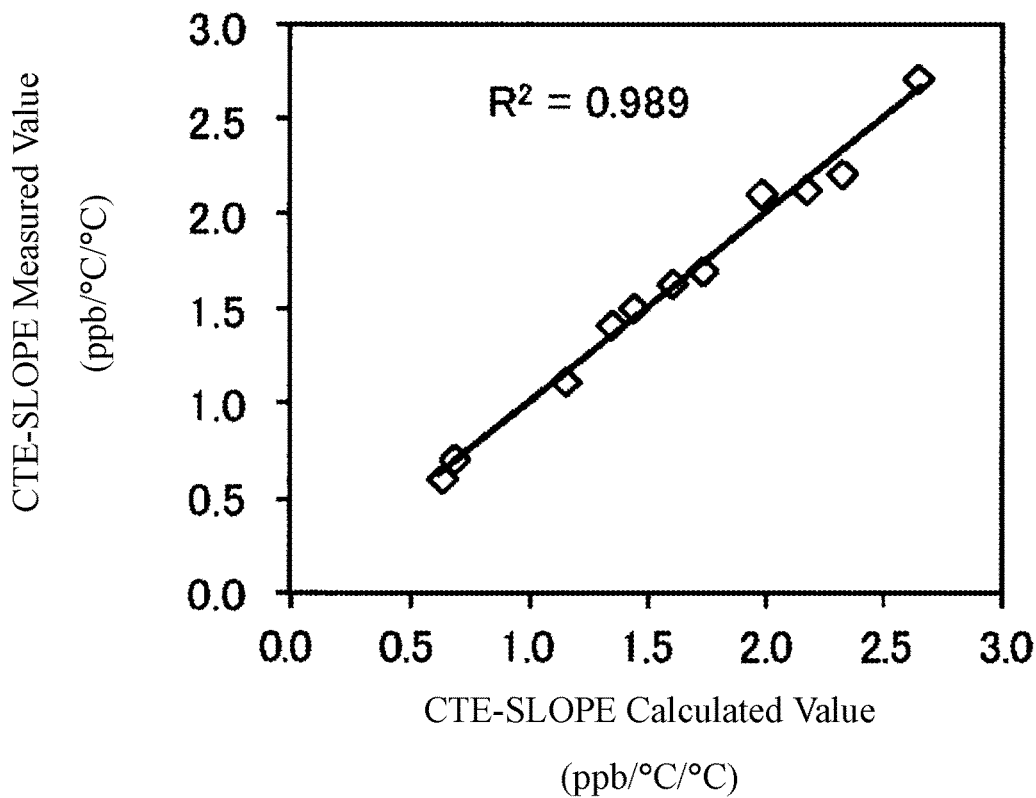
FIG. 4 is a graph showing a relationship between a calculated value of CTE-SLOPE calculated by using a linear relational expression and a measured value in Examples.

Table 2 also shows the CTE-SLOPE value calculated from the linear relational expression (2) and the actually measured CTE-SLOPE value at 22° C., and FIG. 4 collectively shows the relationship between the calculated value and the actually measured value in a graph.

From FIGS. 3 and 4, it is found that, in both the CTE value and the CTE-SLOPE value, there is a good correlation between the calculated values calculated from the linear relational expression and the actually measured values.

Hereinafter, COT is calculated and evaluated as a thermal expansion property.

With respect to COT, the above-mentioned linear relational expression (E1) is similarly obtained for a plurality of temperatures other than 22° C. Here, as the temperature Tx, at each of five temperatures of 16° C. for Tx1, 19° C. for Tx2, 22° C. for Tx3, 25° C. for Tx4, and 28° C. for Tx5, a linear relational expression CTE at Tx was obtained.

Figure 5:
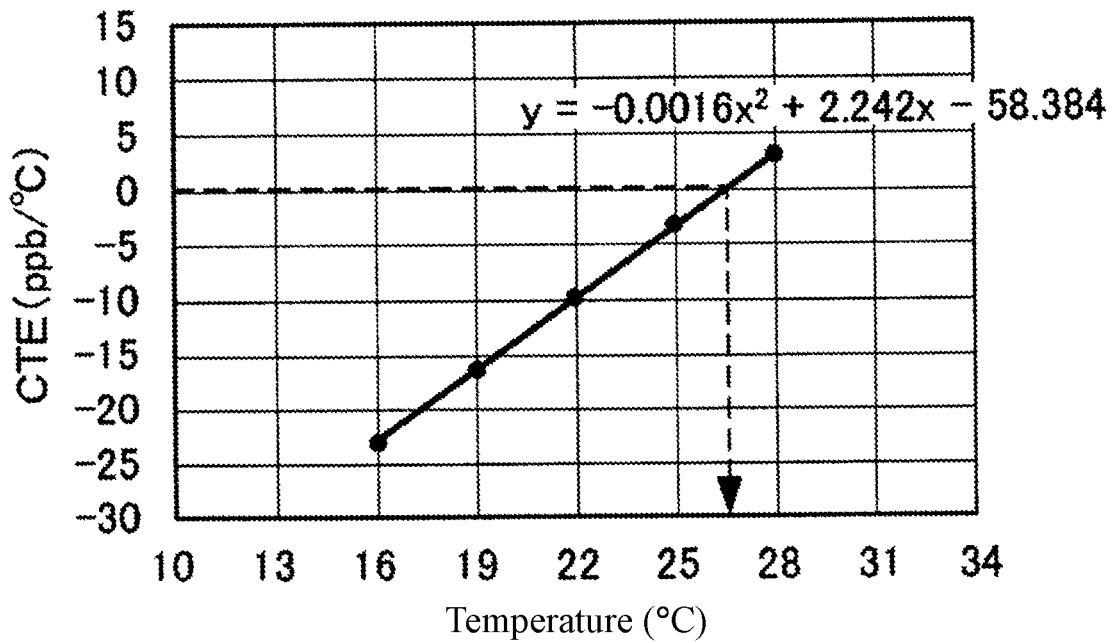
FIG. 5 is a diagram for explaining a method for calculating a calculated value of COT in Examples.

This was applied to each sample (1 to 11), and five CTE values at above-mentioned individual temperatures (Tx1 to Tx5) were determined from the measured values of a plurality of physical parameters. The determined CTE values were fitted as a quadratic function of temperature, and from the quadratic function CTE=a3T$^2$+b3T+c3, a temperature $T_0$ at which CTE became 0 was defined as COT. FIG. 5 shows the relationship between the temperature and CTE in Sample 4.

Figure 6:
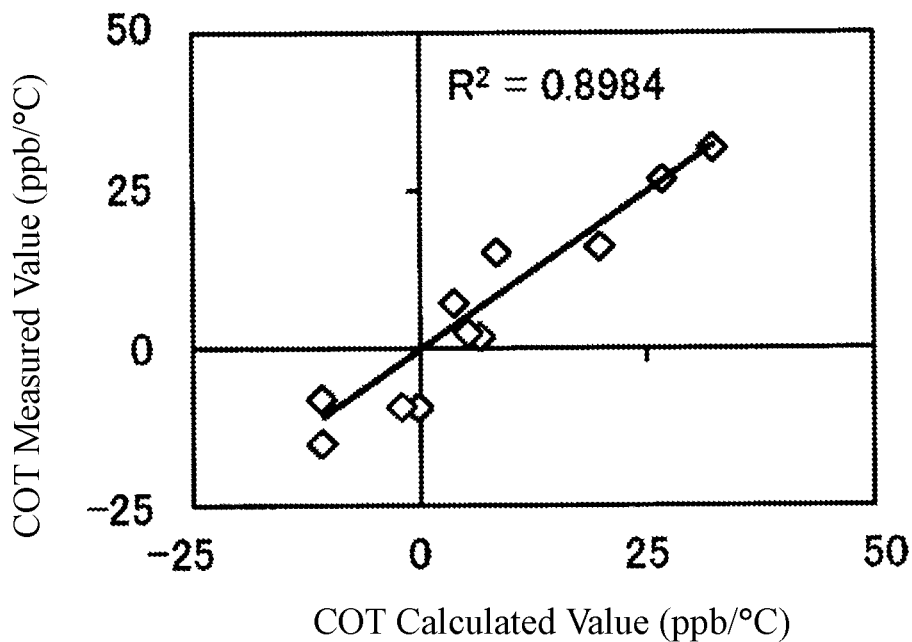
FIG. 6 is a graph showing a relationship between a calculated value of COT calculated by using a linear relational expression and a measured value in Examples.

FIG. 6 shows the relationship between the thus obtained calculated COT and actually measured COT in a graph. From FIG. 6, it was found that there is a good correlation between the calculated values and the actually measured values also with respect to COT, and that the thermal expansion properties of the TiO$_2$—SiO$_2$ glass body can be sufficiently evaluated.

TABLE 2

|  | CTE calculated value (ppb/° C.) | CTE measured value (ppb/° C.) | CTE-SLOPE calculated value (ppb/° C.) | CTE-SLOPE measured value (ppb/° C.) | COT calculated value (° C.) | COT measured value (° C.) |
|---|---|---|---|---|---|---|
| Sample 1 | 45.0 | 52.3 | 2.10 | 1.98 | −10.7 | −8.0 |
| Sample 2 | 10.1 | 3.6 | 1.69 | 1.74 | 19.9 | 16.1 |
| Sample 3 | 93.4 | 91.6 | 2.20 | 2.32 | −10.7 | −14.8 |
| Sample 4 | −10.0 | −9.8 | 2.12 | 2.17 | 26.5 | 26.8 |
| Sample 5 | 56.0 | 50.6 | 2.70 | 2.65 | 5.2 | 2.5 |
| Sample 6 | 69.0 | 61.3 | 1.10 | 1.16 | −2.1 | −9.1 |
| Sample 7 | 61.7 | 57.6 | 1.63 | 1.61 | −0.5 | −9.1 |
| Sample 8 | 38.1 | 50.6 | 1.50 | 1.45 | 3.7 | 6.8 |
| Sample 9 | 10.0 | 23.0 | 1.41 | 1.35 | 8.5 | 15.2 |
| Sample 10 | −5.0 | −5.1 | 0.61 | 0.65 | 32.4 | 31.8 |
| Sample 11 | 26.0 | 18.7 | 0.70 | 0.69 | 6.5 | 2.0 |

As described above, according to the present embodiment, it was found that, for a $TiO_2$—$SiO_2$ glass body to be a target, the thermal expansion properties such as CTE, CTE-SLOPE and COT can be easily evaluated by non-destructive measurement.

While the present invention has been described in detail and with reference to specific embodiments thereof, it will be apparent to one skilled in the art that various changes and modifications can be made therein without departing from the spirit and scope of the present invention. The present application is based on Japanese Patent Application (No. 2017-247630) filed on Dec. 25, 2017, and the contents thereof are incorporated herein by reference.

INDUSTRIAL APPLICABILITY

According to the present invention, the thermal expansion properties of CTE and CTE-SLOPE of a $TiO_2$—$SiO_2$ glass body can be evaluated more simply and in a shorter time as compared with the case of using an absolute dilatometer. Furthermore, the thermal expansion properties of an arbitrary portion in a parallel plane can be non-destructively evaluated for a product itself of an optical material for an EUVL exposure apparatus.

The invention claimed is:

1. A method for evaluating thermal expansion properties of a glass body, the glass body comprising a $TiO_2$—$SiO_2$ glass or a fluorine doped $TiO_2$—$SiO_2$ glass, the method comprising:
    measuring a longitudinal wave sound velocity or transverse wave sound velocity of the glass body at a predetermined temperature $T_x$;
    obtaining a Raman spectrum of the glass body;
    analyzing the Raman spectrum to determine a ratio value $I_1/I_0$ or $I_2/I_0$ wherein a peak intensity at 440 $cm^{-1}$ or 820 $cm^{-1}$ is denoted by $I_0$, a scattered peak intensity at 495 $cm^{-1}$ is denoted by $I_1$, and a peak intensity at 605 $cm^{-1}$ is denoted by $I_2$, and
    to determine a ratio value $I_3/I_0$ or $I_4/I_0$ when the peak intensity at 440 $cm^{-1}$ or 820 $cm^{-1}$ is denoted by $I_0$, a peak intensity at 960 $cm^{-1}$ is denoted by $I_3$ and a peak intensity at 1.140 $cm^{-1}$ is denoted by $I_4$;
    calculating the coefficient of thermal expansion and/or the slope of the coefficient for thermal expansion by inserting the measured physical parameters obtained in equations (1) and/or (2);

$$\text{CTE at } Tx = a1[A] + b1[B] + c1[C] + d1 \quad (1),$$

$$\text{CTE-SLOPE at } Tx = a2[A] + b2[B] + c2[C] + d2 \quad (2)$$

wherein
    [A] is a term containing a longitudinal wave sound velocity $V_L$ or a transverse wave sound velocity $V_S$ in the glass body;
    [B] is a term containing $I_1/I_0$ or $I_2/I_0$;
    [C] is a term containing $I_3/I_0$ or $I_4/I_0$; and a1, b1, c1, d1, a2, b2, c2, and d2 ore coefficients calculated by regression calculation by a least-square method from the relational expressions (1) and (2) employing $TiO_2$—$SiO_2$ glass or a fluorine doped $TiO_2$—$SiO_2$ glass samples of known composition using values of CTE and CTE-slope obtained by direct measurement.

2. The method for evaluating thermal expansion properties of a glass body, according to claim 1,
    wherein the glass body comprises at least one pair of opposing parallel planes, one plane of the at least pair of opposing parallel planes has an area of 200 $cm^2$ to 3,000 $cm^2$, and a distance between the one pair of opposing parallel planes is in a range of 0.5 cm to 15 cm.

3. The method for evaluating thermal expansion properties of a glass body, according to claim 1,
    wherein the glass body is a photomask substrate.

4. The method for evaluating thermal expansion properties of a glass body, according to claim 1,
    wherein the predetermined temperature Tx is within a temperature range of from 0° C. to 60° C.

5. The method for evaluating thermal expansion properties of a glass body, according to claim 1,
    wherein the predetermined temperature Tx is within a temperature range of from 5° C. to 50° C.

6. The method for evaluating thermal expansion properties of a glass body, according to claim 1,
    wherein the predetermined temperature Tx is within a temperature range of from 15° C. to 40° C.

7. A method for manufacturing a $TiO_2$—$SiO_2$ glass or a fluorine doped $TiO_2$—$SiO_2$ glass photomask substrate, comprising:
    molding a transparent glass body of a $TiO_2$—$SiO_2$ lass or a fluorine doped $TiO_2$—$SiO_2$ glass to obtain a molded glass body in the form of the photomask substrate;
    determining the CTE and CTE-Slope of the photomask substrate according to the method of claim 1;
    comparing the determined CTE and CTE-SLOPE values to target range values of CTE and CTE-SLOPE for performance as a photomask;
    evaluating whether at least one of the following requirements is satisfied:
    i) the CTE falls within the target CTE range; and
    ii) the CTE-SLOPE is a target value or less; and
    selecting the glass body as an acceptable photomask substrate in a case where at least one of the requirements i) and ii) is satisfied.

8. The method according to claim 7, wherein the $TiO_2$—$SiO_2$ glass or fluorine doped $TiO_2$—$SiO_2$ glass photomask substrate comprises at least one pair of opposing parallel planes, one plane of the at least one pair of opposing parallel planes has an area of 200 $cm^2$ to 3,000 $cm^2$, and a distance between the one pair of opposing parallel planes is in a range of 0.5 cm to 15 cm.

* * * * *